US008288307B2

(12) United States Patent
Quinn et al.

(10) Patent No.: US 8,288,307 B2
(45) Date of Patent: Oct. 16, 2012

(54) MECHANICAL ALLOYING OF A HYDROGENATION CATALYST USED FOR THE REMEDIATION OF CONTAMINATED COMPOUNDS

(75) Inventors: Jacqueline W. Quinn, Titusville, FL (US); Christian A. Clausen, Chuluota, FL (US); Cherie L. Geiger, Geneva, FL (US); Brian S. Aitken, Satellite Beach, FL (US)

(73) Assignee: The United States of America as Represented by the Administrator of the National Aeronautics and Space Administration, Washington, DC (US)

( * ) Notice: Subject to any disclaimer, the term of this patent is extended or adjusted under 35 U.S.C. 154(b) by 0 days.

(21) Appl. No.: 12/909,219

(22) Filed: Oct. 21, 2010

(65) Prior Publication Data
US 2011/0172082 A1    Jul. 14, 2011

Related U.S. Application Data

(62) Division of application No. 11/749,767, filed on May 17, 2007, now Pat. No. 7,842,639.

(60) Provisional application No. 60/747,681, filed on May 19, 2006.

(51) Int. Cl.
*B01J 23/00* (2006.01)
*B01J 21/00* (2006.01)

(52) U.S. Cl. ........ 502/182; 502/183; 502/184; 502/185; 502/300; 502/326; 502/328; 502/338; 502/339; 502/340; 502/439

(58) Field of Classification Search .................. 502/300, 502/338, 339, 439, 182–185, 326, 328, 340
See application file for complete search history.

(56) References Cited

U.S. PATENT DOCUMENTS

| 3,986,953 A | 10/1976 | Beaucaire |
| 4,186,110 A * | 1/1980 | Jalan et al. ............ 502/101 |
| 4,425,261 A | 1/1984 | Stenius |
| 4,450,244 A * | 5/1984 | Domesle et al. ............ 502/185 |
| 4,565,635 A | 1/1986 | Le Du |
| 4,918,218 A * | 4/1990 | Mueller et al. ............ 560/232 |

(Continued)

FOREIGN PATENT DOCUMENTS
EP   0409172 A2   1/1991
(Continued)

OTHER PUBLICATIONS

Gieger et al., "The In situ Treatment of DNAPL with Zero-Valent Iron Emulsions", The 2001 International Containment & Remediation Technology Conference, presented Jun. 12, 2001, 3 pages.

(Continued)

*Primary Examiner* — Cam N. Nguyen
(74) *Attorney, Agent, or Firm* — Randall Heald; Michelle Ford; Jennifer Yancy

(57) ABSTRACT

A hydrogenation catalyst including a base material coated with a catalytic metal is made using mechanical milling techniques. The hydrogenation catalysts are used as an excellent catalyst for the dehalogenation of contaminated compounds and the remediation of other industrial compounds. Preferably, the hydrogenation catalyst is a bimetallic particle including zero-valent metal particles coated with a catalytic material. The mechanical milling technique is simpler and cheaper than previously used methods for producing hydrogenation catalysts.

11 Claims, 2 Drawing Sheets

U.S. PATENT DOCUMENTS

| | | | | |
|---|---|---|---|---|
| 4,983,217 | A | 1/1991 | Lopez Quintela | |
| 5,147,841 | A | 9/1992 | Wilcoxon | |
| 5,149,680 | A * | 9/1992 | Kitson et al. | 502/185 |
| 5,265,674 | A | 11/1993 | Fredrickson | |
| 5,266,213 | A | 11/1993 | Gillham | |
| 5,278,106 | A | 1/1994 | Nakashima | |
| 5,449,655 | A * | 9/1995 | Albers et al. | 502/185 |
| 5,587,157 | A | 12/1996 | Cox | |
| 5,615,974 | A | 4/1997 | Land | |
| 5,631,044 | A | 5/1997 | Rangaswamy | |
| 5,641,425 | A | 6/1997 | McKedy | |
| 5,725,802 | A | 3/1998 | Chittofrati | |
| 5,733,067 | A | 3/1998 | Hunt | |
| 5,746,937 | A | 5/1998 | McKedy | |
| 5,759,389 | A | 6/1998 | Fernando | |
| 5,783,514 | A * | 7/1998 | Schick et al. | 502/185 |
| 5,789,649 | A | 8/1998 | Batchelor | |
| 5,833,388 | A | 11/1998 | Edwards | |
| 5,857,810 | A | 1/1999 | Cantrell | |
| 5,868,939 | A | 2/1999 | Oder | |
| 5,916,840 | A * | 6/1999 | Ebner et al. | 502/331 |
| 5,975,798 | A | 11/1999 | Liskowitz | |
| 5,990,365 | A | 11/1999 | Chang | |
| 6,013,232 | A | 1/2000 | Quinn | |
| 6,039,882 | A | 3/2000 | Wolfe | |
| 6,102,621 | A | 8/2000 | Siegrist | |
| 6,121,371 | A | 9/2000 | Matyjaszewski | |
| 6,168,775 | B1 * | 1/2001 | Zhou et al. | 423/584 |
| 6,190,092 | B1 | 2/2001 | Miller | |
| 6,207,114 | B1 | 3/2001 | Quinn | |
| 6,217,779 | B1 | 4/2001 | Orth | |
| 6,261,029 | B1 | 7/2001 | Miller | |
| 6,264,399 | B1 | 7/2001 | Grisso | |
| 6,265,205 | B1 | 7/2001 | Hitchens | |
| 6,280,533 | B1 | 8/2001 | Hoppe | |
| 6,284,213 | B1 * | 9/2001 | Paparatto et al. | 423/403 |
| 6,357,968 | B1 | 3/2002 | Dwyer | |
| 6,398,960 | B1 | 6/2002 | Borden | |
| 6,413,489 | B1 | 7/2002 | Ying | |
| 6,417,133 | B1 * | 7/2002 | Ebner et al. | 502/185 |
| 6,423,531 | B1 | 7/2002 | Hince | |
| 6,432,866 | B1 * | 8/2002 | Tennent et al. | 502/180 |
| 6,492,299 | B1 * | 12/2002 | Couves et al. | 502/339 |
| 6,537,944 | B1 * | 3/2003 | Zoeller et al. | 502/180 |
| 6,664,298 | B1 | 12/2003 | Reinhart | |
| 6,686,308 | B2 * | 2/2004 | Mao et al. | 502/180 |
| 6,689,505 | B1 * | 2/2004 | Albers et al. | 429/480 |
| 6,734,144 | B2 | 5/2004 | Varadaraj | |
| 6,746,597 | B2 * | 6/2004 | Zhou et al. | 208/138 |
| 6,753,290 | B1 * | 6/2004 | Romanenko et al. | 502/185 |
| 6,861,387 | B2 * | 3/2005 | Ruth et al. | 502/184 |
| 6,903,046 | B2 * | 6/2005 | Ding | 502/185 |
| 6,919,065 | B2 * | 7/2005 | Zhou et al. | 423/584 |
| 7,008,964 | B2 | 3/2006 | Clausen | |
| 7,037,946 | B1 | 5/2006 | Reinhart | |
| 7,060,385 | B2 * | 6/2006 | Kato et al. | 429/524 |
| 7,108,939 | B2 * | 9/2006 | Suzuki et al. | 429/532 |
| 7,109,145 | B2 * | 9/2006 | Ruth et al. | 502/326 |
| 7,132,385 | B2 * | 11/2006 | Pak | 502/185 |
| 7,186,668 | B2 * | 3/2007 | Werpy et al. | 502/180 |
| 7,279,590 | B2 | 10/2007 | Inukai | |
| 7,462,575 | B2 * | 12/2008 | Hommura et al. | 502/185 |
| 7,468,340 | B2 * | 12/2008 | Ohya et al. | 502/180 |
| 7,569,508 | B2 * | 8/2009 | Zhou et al. | 502/150 |
| 7,572,427 | B2 * | 8/2009 | Nagy et al. | 423/447.3 |
| 7,618,919 | B2 * | 11/2009 | Shimazu et al. | 502/439 |
| 7,659,225 | B2 * | 2/2010 | Chen et al. | 502/182 |
| 7,713,911 | B2 * | 5/2010 | Wakamatsu et al. | 502/332 |
| 7,824,771 | B2 * | 11/2010 | Im et al. | 428/408 |
| 7,875,250 | B2 * | 1/2011 | Nunan | 422/177 |
| 2002/0061352 | A1 | 5/2002 | Ekanayake | |
| 2002/0151602 | A1 | 10/2002 | Vance | |
| 2004/0053050 | A1 | 3/2004 | Guerfi | |
| 2004/0069720 | A1 | 4/2004 | Clausen | |
| 2005/0208380 | A1 | 9/2005 | Park | |

FOREIGN PATENT DOCUMENTS

| | | |
|---|---|---|
| EP | 1508571 A1 | 2/2005 |
| WO | WO9709114 | 3/1997 |
| WO | WO0240409 A1 | 5/2002 |

OTHER PUBLICATIONS

Geiger et al, "The In Situ Treatment of DNAPL with Zero-Valent Iron Emulsions", found with Google.com search Feb. 27, 2003, undated, 27 pages.

Environmental Technologies, Inc, "Permeable Reactive Barrier Update", May 2000, from www.eti.ca, 4 pages.

Center for Groundwater Research "Zero Valent Iron", from http://cgr.ese.ogi,edu/iron/iron, date unknown, 4 pages.

AFCEE, Lee and Borden, "Technology Application of Low Cost Emplacement of Insoluble Organic Substrate for Enhanced In Situ Reductive Dechlorination of halogenated Aliphatic Hydrocarbons: Dover Air Force Base, Delaware", Oct. 28, 1999, 6 pages.

Abstract: In-Situ Reductive Dehalogenation of DNAPLS by the Use of Enulsified Zero-Valent Nanoscale Iron particles, 1999 NASA STTR Phase 1 Proposal #990094, using www.google.com at the website http://www.spacepda.net/abstracts/99/sttr_html/02-990094.htm, 1 page.

Kaplan et al., "Formation of a barrier to groundwater contaminants by injection of zero-valent iron colloids: suspension properties," Proc. In Situ Remediation: Scientific Basis for Current and Future Technologies Symposium. Presented at the thirty-third Hanford Symposium on Health and the Environment; Nov. 7-11, 1994. 17 pages.

Wang Chuan-Bao et al., "Synthesizing Nanoscale Iron Particles for Rapid and Complete Dechlorination of TCE and PCBs". Environmental Science & Technology, vol. 31, No. 7, pp. 2154-2156 (1997).

Ghosh, Rajat S., "State of SERDP/ESTCP Funded Zero-Valent Iron (ZVI) Research and Technology", SERDP, 21 pages, from www.frtr.gov/pdf/meetings/k-ghosh_09jun04.pdf, undated, 21 pages.

NASA, Technology Opportunity Showcase, "Emulsified Zero-Valent Iron (EZVI)" downloaded from www.ipp.nasa.gov/innovation/innovation111/7-techop2.html, 1 page.

Quinn et al., "Field Demonstration of DNAPL Dehalogenation Using Emulsified Zero-Valent Iron". Environmental Science & Technology, vol. 39, No. 5, pp. 1309-1318 (2005).

O'hara et al., Emulsified Zero-Valent Iron Treatment of Chlorinated Solvent DNAPL Source Areas from http://rtdf.org/PUBLIC/permbarr/minutes/101603/pdf/n_ohara.pdf see pp. 7-9 especially; 30 pages.

Summary of the Remediation Technologies Development Forum Permeable Reactive Barriers Action Team Meeting, Jun. 12, 2001, http://www.rtdf.org/public/permbarr/minutes/061201.htm, 24 pages.

NASA, Technical Opportunity Sheet, "Emulsified Zero-Valent Iron (EZVI)", Released Aug. 2002, 2 pages.

* cited by examiner

MECHANICAL ALLOYING OF A HYDROGENATION CATALYST USED FOR THE REMEDIATION OF CONTAMINATED COMPOUNDS

CROSS-REFERENCE TO RELATED APPLICATIONS

The application is a divisional application claiming the benefit of U.S. patent application Ser. No. 11/749,767 filed on May 17, 2007, which issued as U.S. Pat. No. 7,842,639 on Nov. 30, 2010, which further claims the benefit, under 35 U.S.C. §119(e), of U.S. Provisional Application Ser. No. 60/747,681 filed May 19, 2006, the contents of which are incorporated herein by reference.

ORIGIN OF INVENTION

The invention described herein was made in the performance of work under a NASA contract and by an employee of the United States Government and is subject to the provisions of Public Law 96-517 (35 U.S.C. §202) and may be manufactured and used by or for the Government for governmental purposes without the payment of any royalties thereon or therefore.

BACKGROUND OF THE INVENTION

1. Field of the Invention

The present invention relates to a method for making a hydrogenation catalyst having a base material coated with a catalytic metal using mechanical milling techniques. This method produces a hydrogenation catalyst that may be used for the remediation of a plurality of contaminated materials, including, but not limited to, polychlorinated biphenyls.

2. Description of Related Art

The class of 209 aromatic chlorinated molecules resulting from the attachment of up to ten chlorine atoms to a biphenyl is collectively known as polychlorinated biphenyls (PCBs). Generally, PCBs are known to have the chemical structure $C_{12}H_{10-n}Cl_n$ and, in addition to other chlorinated synthetic aromatic compounds, are of great concern due to their toxicity and persistence in the environment. Among the properties of these synthetic colorless liquids are high chemical stability, low flammability, low thermal and electrical conductivity, and low solubility in water.

Twenty-nine years following the 1976 Toxic Substances Control Act (TSCA) ban on their manufacture, PCBs remain a continued environmental threat. Their persistence owes to the very high chemical stability of these molecules. Prior to the TSCA ban, these favorable properties were exploited in a variety of applications including paint stabilizers, transformer oils, capacitors, printing inks, and pesticides.

Toxicity evidence was found adequate to justify TSCA regulation; however, the debate over the extent of PCB toxicity on organisms remains heated. PCBs are known to bioaccumulate and concentrate in fatty tissues. Studies suggest increased incidences of cancer with long-term PCB exposure. These studies are arguably inconclusive as they involve the simultaneous analysis of multiple congeners. Further complications arise from the potential for contamination of commercial mixtures with other more toxic chlorinated compounds such as polychlorinated dibenzodioxins (PCDDs) and polychlorinated dibenzofurans (PCDFs).

Until recently, only one option was available for the treatment of PCB-contaminated materials, incineration. This, however, may prove to be more detrimental to the environment than the PCBs themselves due to the potential for formation of PCDDs. PCDDs have been shown to exist at abnormally high levels in proximity to incinerators burning chlorine-contaminated materials. Cancer rates have also been "well correlated" to both dioxins and proximity to chlorine-contaminated waste burning incinerators. The temperature required to incinerate PCB-contaminated material may be up to 1200° C. Additionally, it is expensive to incinerate the PCB-contaminated material and to transport contaminated material.

An alternate approach that has been used to treat PCB-contaminated materials is bioremediation. This is accomplished by the reductive dechlorination of PCBs by anaerobic microorganisms. However, this usually results in an incomplete removal of PCBs. Furthermore, specific conditions are required for bioremediation and are not always seen in contaminated sites.

Solvent extraction has also been used to treat PCB-contaminated materials. Organic solvents are used to extract contaminated matrix. However, extraction is only applied ex-situ and the PCBs are not actually destroyed but transported to another media that has to be further treated.

Base-catalyzed decontamination has been used to treat PCB-contaminated material by adding $NaHCO_3$ or NaOH to the media. However, this remediation process is only applied ex-situ due to operating temperatures.

Metals have been used for the past 10 years for the remediation of halogenated solvents and other contaminants in the environment; however, zero-valent metals alone do not possess the activity required to dehalogenate PCBs.

Recent literature reports the rapid and complete reductive dechlorination of PCBs using palladium coated iron (Pd/Fe) or magnesium (Pd/Mg) in aqueous medium. The use of these bimetallic particles for dechlorination relies on the reduction potentials of magnesium or iron coupled with the hydrogenation-type catalytic activity of palladium. The current techniques for preparing Pd/Fe material provides for the easy preparation of the material using pallameres. Although the Pd/Mg material has a greater thermodynamic driving force and forms a self-limiting oxide layer to prevent extensive air oxidation, this material cannot be easily prepared with pallamerse. Therefore, a process for making palladized zero-valent metals using cost-effective and efficient techniques would be valuable.

Comminution theory is principally concerned with reducing the average size of particles in a sample of crystalline or metallic solid; however, it can also be used to understand mechanical alloying of particles. To accomplish either of these tasks, the most commonly used processes involve ball milling, vibrational milling, attrition, and roller milling.

Ball milling is a process in which a material is loaded into a canister partially filled with milling balls. The canister is then rotated at high speed on its major axis so that the balls are held by centripetal force to the inside wall until they reach the highest point inside the canister. Gravitational force then exceeds the upward force of the balls and they fall to the bottom of the canister where they impact other balls and the canister wall.

If some milling material is pinched between the participants in one of these collisions and the collision is of adequate energy, then the particles are fractured into smaller particles. It should also be noted that a certain critical speed of rotation is necessary for this process to occur. At lower speeds the balls will simply roll over one another and at extremely high speeds their upward force will exceed gravity at all points inside the canister and the balls will stick to the canister wall. The approximate critical speed of any ball mill is given below and is usually on the order of about 250 RPMs, $$N_c = 7.05/(D^{1/2})$$

where $N_c$=critical speed and D=milling canister diameter

Vibrational milling is a process similar to ball milling except that the milling vessel is vigorously shaken in a back and forth motion or in a back in forth motion in conjunction with a lateral motion that produces a "figure 8" path. This type of milling relies solely on the extremely high-energy collisions between rapidly moving milling balls rather than the collisions between the balls and the canister wall, as described for ball milling. Since vibrator mills can often shake canisters at a rate of approximately 1200 RPMs, often producing ball speeds of upwards of 5 m/s, vibrational milling commonly yields the desired reduction in particle size at a rate one order of magnitude faster than that of ball milling.

Two other less common types of milling are attrition milling and roller milling. These processes are not commonly seen in laboratory settings but are often seen in industrial work. Attrition milling relies on rapidly spinning paddles to stir the milling balls present in the milling vessel. The rate of size reduction observed is often similar to the rate of reduction observed for vibrator mills of similar size; however, due to the necessity of a cooling system this type of milling is often limited in its capabilities to systems that can be milled in liquid media.

Roller milling is a process that relies on fracturing caused by stress induced in the system from the compression of materials between two rolling bars or cylinders. It is most often used for reduction of very coarse materials into less coarse materials that can later be reduced in size by other means. The previous two systems are not discussed quantitatively.

For all milling types (other than roller milling), the reduction of particle size relies on stresses induced in individual particles caused by collisions within the milling vessel. This process reduces the average particle size until equilibrium is reached, at which point no further size reduction is observed. This phenomenon can be explained if one considers crystal matrix impurities as the cause of fracture. As each fracture occurs at the point or plane of an impurity that disrupts the crystal structure, that particular discontinuity disappears, thus the average number of imperfections in the crystal structure of each particle in the sample reduces. Since the crystal structure of each particle in the sample becomes more perfect each time a fracture occurs, at some point the particles will exhibit a near perfect crystalline structure. At this time, the collisions within the mill will no longer be of adequate energy to cause fracture and the size equilibrium will be reached.

Another explanation for this phenomenon arises from the fact that it is more difficult to inflict upon smaller particles the necessary sheer required to cause fracture. This can be explained by the observation that the probability of a milling ball impacting a particle with the necessary directional velocity is reduced when the particle is smaller. Additionally, smaller particles have a higher surface activity and therefore, have a greater probability of being re-welded to form larger particles.

The equilibrium size of the particles in a milling batch has been the topic of much research and one of the more straightforward methods for calculating this size, based on a number of variables, follows and can be applied to all types of milling:

W=mass of particles with surface area$\leq S$ $$W_i(t) = \sum_{j=1}^{i} a_{ij} e^{-S_j t} \text{ where}$$

$$a_{ij} = \begin{bmatrix} 0 & \text{for } i < j \\ W(0) - \sum_{k=1}^{i-1} a_{ik} & \text{for } i = j \\ \frac{1}{S_i - S_j} \sum_{k=j}^{i-1} S_k b_{ik} a_{kj} & \text{for } i > j \end{bmatrix}$$

$$B_{ij} = \psi(x_j/x_k)^\delta (x_j/x_i)^\beta + (1-\psi)(x_j/x_1)^\delta (x_j/x_i)^\gamma$$

$$S_j = K(x_j/x_1)^\alpha$$

To use this equation, the desired mass of reduced size particles and the size of these particles is specified to yield the milling time required for achieving these parameters. Solving this series however, involves the use of many constants, which must be determined through calibration experiments using materials for which the constants are already known.

In other areas of research, such as mechanical activation of reactants in a milling vessel, researchers are focused more on the rate of particle size reduction as opposed to the average particle size of the end product. In general, the rate at which a mill reduces the average size of the particles being milled is a function of the probability of any particle being trapped between the participants in the above stated types of collisions when those collisions possess the energy necessary to fracture a particle. This focus has produced a number of functions, which have been supported empirically, to determine the rate of particle size reduction. A few of the more general examples are shown below for ball milling and vibrational milling.

In terms of the change in total surface area of materials
For Ball Milling $$\text{for } U \leq 1 \quad M \frac{dS}{dt} = 0.50 k_1 K' \phi L J d^{-1.7} D^{2.2} x^{B+1} U \left[ 1 - 1.1 \sigma_a \left( \frac{k_1 x U}{Y \rho_B d D} \right)^{1/2} \right]^{1.5}$$

$$\text{for } U > 1 \quad M \frac{dS}{dt} = 1.1 k_2 K' \phi L J d^{-2.2} D^{2.7} x^{B+1} \left\{ 1 - 1.1 \sigma_a \left[ \frac{(U+k_1-1)x}{Y \rho_B d D} \right]^{1/2} \right\}^{1.5}$$

For Vibrational Milling $$M \frac{dS}{dt} = 0.6 k_1' K' J^2 L D^2 d^{-2} \alpha \omega \theta x^{B+1} U \left[ 1 - 230 \sigma_a' \left( \frac{k_1' x U}{Y \rho_B d \alpha^2 \omega^2} \right)^{1/2} \right]^{1.5}$$

These equations are applicable only when $U \leq 1$.
where,
U=volume of particles in mill/(volume of mill−volume of balls)
n=$0.4 d^3 x^{-3} U$
n=number of particles per ball, dimensionless
S=specific surface of particles, sq.cm./g.$_m$
φ=ratio of mill speed to critical one, dimensionless
L=length of mill, cm.

J=fractional ball filling of mill, dimensionless
d=diameter of ball, cm.
D=diameter of mill, cm.
x, x'=particle size, cm.
Y=modulus of elasticity of materials, g./sq.cm.
and all other terms are constants relating to the material being milled Since these equations are often difficult to use, empirical studies of milling variables may prove to be more useful.

In general, it can be seen that the rate of particle reduction in vibrational milling is much greater than in ball milling. Additionally, for all types of milling, rate increases with ball density and is greatest when the mill filling ratio (volume of material to be milled/volume of mill) is approximately 10-20% while the volume occupied by milling balls is approximately 40-60% of the total mill volume.

In the case where one wishes to mechanically alloy materials, the previously discussed theories apply, however several additional topics must also be considered. Mechanical alloying is a high-energy milling process for producing composite materials with an even distribution (though not homogeneous in the rigorous sense) of one material into another. By definition, at least one of the materials must be metallic to be considered an alloy; however, the topics discussed here can be applied to non-metallic materials as well. Two systems will be discussed; Malleable-Malleable and Brittle-Malleable.

In a malleable-malleable system such as the milling of two soft materials, like sodium and gold, ball-powder-ball collisions initially reduce the size of both materials until the average active surface area of each particle in the sample is large enough for re-welding to occur. When this critical surface area is achieved, in a particle, re-welding can occur between two similar particles or two dissimilar particles. If re-welding occurs between two similar particles, the net process results in no change of the material nature. If re-welding occurs between two dissimilar particles an alloy particle is created. This alloy particle can then undergo further fragmentation along alternative planes and subsequently be re-welded multiple times. The longer this process is allowed to take place, the more dissolved one material becomes in the other.

In a brittle-malleable system such as palladium and magnesium, the more ductile magnesium is initially flattened while fragmentation of the more brittle palladium occurs. With further milling, the ductile material occludes brittle fragments leading to an individual particle composition of the starting mixture. Depending on the solubility of the brittle phase, continued milling may result in near chemical homogeneity.

These processes can be carried out using any type of mill however the lower energy route, ball milling, will require much longer milling times to produce a well-distributed alloy. This can be easily explained using theories already discussed. Simply put, ball milling produces relatively few collisions, most of which are relatively low in energy, while vibrational milling produces an abundance of very high-energy collisions of grinding material. Since high-energy collisions are necessary for alloying to occur vibrational milling produces the desired result with a greatly enhanced rate.

SUMMARY OF THE INVENTION

The present invention is directed to a method for making a hydrogenation catalyst using mechanical milling techniques. The hydrogenation catalyst includes a base material coated with at least one catalytic metal. The base material is preferably a metallic and/or mineral material. Most preferably, the base material is a zero-valent metal. Hydrogenation catalysts having metallic base materials have been shown to act as an excellent catalyst for the dechlorination of polychlorinated biphenyls (PCBs) and other halogenated aromatic compounds. Although previous methods for plating the base material have been used, these prior methods have proven to be inefficient and not cost effective. It has been discovered that mechanical milling techniques can be used to produce a hydrogenation catalyst capable of dechlorinating PCBs and other halogenated aromatic compounds. The mechanical milling technique is simpler and cheaper than previously used methods for producing hydrogenation catalysts.

Most preferably, the hydrogenation catalyst is a bimetallic particle formed from a zero-valent iron (Fe) or zero-valent magnesium (Mg) particle coated with palladium (Pd) that is impregnated onto a high surface area graphite support. In a preferred embodiment, the zero-valent metal particles are microscale or nanoscale zero-valent magnesium or zero-valent iron particles. Preferably, the microscale particles would have a diameter in the range of 1-3 microns. Whereas, the preferred nanoscale particles would have a diameter in the range of 20-300 nm. It should be understood that other zero-valent metal particles and combinations may be used. Additionally, the base material may be selected from a wide variety of minerals including, but not limited to, alumina and zeolites. The catalytic metal is preferably selected from the group consisting of noble metals and transition metals. The preferred catalytic metal is palladium. The preferred mass percent palladium by weight ranges from approximately 0.08-8%, but higher and lower ranges could still yield positive results. Additional catalysts include, but are not limited to, nickel and zinc impregnated into a high surface area conductive support.

The mechanical milling process includes milling the base material with a catalytic metal impregnated into a high surface area support to form the hydrogenation catalyst. In a preferred mechanical milling process, a zero-valent metal particle is provided as the base material preferably having a particle size of less than about 10 microns, preferably 0.1-10 microns or smaller, prior to milling. In a preferred mechanical milling process, the catalytic metal is supported on a conductive carbon support structure prior to milling. For example, palladium may be impregnated on a graphite support. Other support structures such as semiconductive metal oxides may also be used. The zero-valent metal particle (e.g. microscale magnesium) is preferably ball milled with 1-10% palladium supported on carbon. The preferred mass percent palladium by weight coating the zero-valent metal particle ranges from approximately 0.01-15%, and more preferably 0.08-8%.

U.S. Pat. No. 7,008,964, the contents of which are incorporated herein by reference, discloses a method for using the hydrogenation catalyst for remediating natural resources. However, the hydrogenation catalyst prepared using the present mechanical milling technique may also be used in other remediation methods known in the field of PCB decontamination. Furthermore, it should be understood that other remediation techniques suitable for hydrogenation could benefit from the present hydrogenation catalyst. For example, the present hydrogenation catalyst may be used for remediating industrial chemicals.

BRIEF DESCRIPTION OF THE DRAWINGS

The features and advantages of the present invention will become apparent from the following detailed description of a preferred embodiment thereof, taken in conjunction with the accompanying drawings, in which.

DETAILED DESCRIPTION OF THE INVENTION

Figure 1:
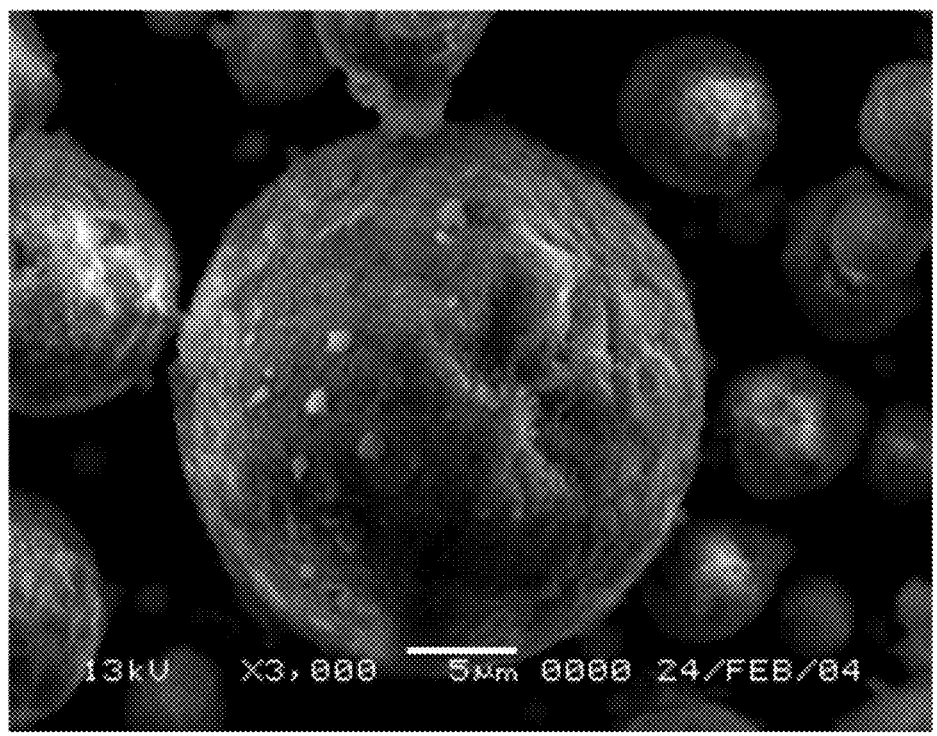
FIG. 1 is an electron micrograph of a bimetallic particle milled for 1.5 hours beyond the optimum milling time.

The present invention is directed to a mechanical milling method for making a hydrogenation catalyst having a base material coated with at least one catalytic metal that is impregnated onto a high surface area support. A variety of mechanical milling techniques may be used including, but not limited to, ball milling, vibrational milling, attrition milling, and roller milling. The hydrogenation catalyst may be used for the dechlorination of chlorinated hydrocarbons, such as polychlorinated biphenyls (PCBs), or for the hydrogenation of other industrial chemicals.

The hydrogenation catalyst is preferably a bimetallic particle formed by mechanically milling a zero-valent metal with a supported catalytic metal to produce a zero-valent metal particle coated with the catalytic metal. Zero-valent metals are known in the industry as metals in their elemental state. Although metallic base materials, such as zero-valent metal particles are preferred, minerals may also be used as the base material. Preferred mineral base materials include, but are not limited to, transition metal oxides. When using the preferred zero-valent metal as the base material, iron or magnesium is preferred. The catalytic metal is preferably palladium. However, it should be understood that other zero-valent metals and catalytic metals, such as nickel and zinc impregnated on a conductive support, may be used. It should be understood to one of ordinary skill in the art that the preferred metallic base material may include other metallic materials other than zero-valent metal particles. Additionally, one of ordinary skill in the art would appreciate that in addition to the formation of bimetallic particles, other multi-metallic particles may also be fabricated using the present mechanical milling technique.

The hydrogenation catalyst is preferably a catalyzed zero-valent metal particle optimized for use in the treatment system and preferably comprises about 0.1% palladium (Pd) impregnated onto a graphite support on zero-valent magnesium (Mg), referred to herein as a Pd/Mg bimetallic. Although, other magnesium-containing bimetallic particles have also been shown to be effective, for example nickel (Ni) supported on graphite and then milled onto magnesium (Mg).

In a preferred embodiment, the hydrogenation catalyst is a bimetallic particle including a zero-valent magnesium metal coated with graphite supported palladium, herein referred to as a Pd/Mg bimetallic, as it has several advantages over other bimetallic particles. However, a second preferred bimetallic particle is a zero-valent iron metal coated with graphite supported palladium. One advantage that the Pd/Mg bimetallic has over other bimetallic particles is the ability to dechlorinate in the presence of oxygen. The zero-valent magnesium or iron acts as a reductant (electron donor) for the removal of chlorine thus, another advantage arises from the greater thermodynamic driving force of magnesium versus iron, as demonstrated by a comparison of reduction potentials:

$$Mg^{2+}+2e^- \rightarrow Mg^0 \quad E^0=-2.20V \text{ vs. SHE}$$

$$Fe^{2+}+2e^- \rightarrow Fe^0 \quad E^0=-0.44V \text{ vs. SHE}$$

Classically, the preferred graphite supported palladium catalyst acts as a hydrodehalogenation catalyst by dissociating hydrogen gas (formed from the reaction of $Mg^0$ or $Fe^0$ with water or another proton donor), that is adsorbed onto the palladium surface, to produce atomic hydrogen. The following is the proposed dechlorination reaction:

$$M^0+2H_2O \rightarrow M^{2+}+H_2+2OH^-$$

or, $$M^0+2HOR \rightarrow M^{2+}H_2+2RO^-$$

$$2RCl+2H.\text{(dissociated on catalyst surface)} \rightarrow 2RH+Cl_2$$

The overall reaction may be expressed as followed $$C_{12}H_xCl_y(aq)+(x+y)M^0(s)+(x+y)H^+(aq) \rightarrow C_{12}H_{10}(aq)+(x+y)M^{2+}(s)+(x+y)Cl^-(aq)$$

In this scheme the reaction products are biphenyl and chloride ions, however, the mechanism for hydrodehalogenation of PCBs to biphenyl by these bimetallic particles has not yet been fully determined. Recent studies, though, have concluded that the process is step-wise. Additionally, some studies have shown that decomposition of biphenyl is possible.

Previous attempts to prepare bimetallic particles relied on electro-deposition to provide the desired bimetallic particle. For example, bimetallic particles were previously prepared by the deposition of palladium onto the magnesium surface by reaction of zero-valent magnesium with palladium acetate. However, to produce reasonable kinetics in this previous technique, a 4% palladium coating was required. Since this was not cost effective, mechanical alloying was attempted.

The following Examples are preferred embodiments for making a Pd/Mg bimetallic using a mechanical milling technique. However, it should be understood that a hydrogenation catalyst may be made including different base materials and catalytic metals supported on a conductive media as provided herein using similar mechanical milling techniques without departing from the scope of the present invention. Furthermore, the Examples provide a preferred embodiment of mechanical milling that may be varied by one of ordinary skill in the art. Not only may other mechanical milling techniques be used, but other operating conditions may be used to provide a hydrogenation catalyst in accordance with the present invention.

EXAMPLE

Small-Scale

The first attempts at producing active mechanically alloyed Pd/Mg bimetallic were carried out using a Spex Centiprep 8000 high-energy vibrator mill. Ball-to-mass ratios and loading levels were not considered while semi-optimizing the process. Milling time and percent palladium were the only variables considered. Using 6 g total mass milling material with three 10 g stainless steel milling balls in a 54.5 mL. Tungsten Carbide milling vessel filled under $N_2$ was found to be the optimum condition for producing the Pd/Mg bimetallic.

The dechlorination ability of the bimetallic particles was analyzed for optimization. Crimp top vials were set up with 1 g neat bimetallic particles and 10 mL 6 ppm Arochlor 1260 water solution. The system was allowed to react for a given time and extracted in hexane. The extraction method was conducted by placing the samples in an ultrasound bath for 30 minutes prior to the extraction. 5 mL of hexane was added to the vial. The vial was then placed in the ultrasound bath for an additional 30 minutes. The vials were removed from the bath and centrifuged for 1 minute. The hexane layer (5 mL) was drawn off. All the samples were then dried with $Na_2SO_4$.

The biphenyl production was monitored over time using GC-FID. However, the PCB remediation was difficult to quantify because biphenyl has been shown to breakdown in this system. Therefore, the results were qualitative at best.

A 1% Pd on graphite was found to be more cost effective with comparable activity for a given bimetal composition. Optimum bimetallic particle composition was found to include 0.083% Pd. Optimum milling time was found to be 3 minutes. For the purposes of producing a catalytically activated Pd/Mg bimetallic, relatively short milling times were initially used, with the high-energy vibrator mill previously described, to avoid complete dissolution of the small quantity of brittle palladium into the large quantity of malleable magnesium. It was then determined after several attempts at producing active material that six grams of bimetal (0.083% Palladium:99.917% Magnesium), matched the reactivity of a (4% Palladium:96% Magnesium) bimetal produced from the electro-deposition described above. The bimetallic particle produced using the mechanical milling technique appeared to work as well or better than bimetallic particles prepared from pallamerse. This was much more economical, however mass production of the bimetallic particle was impossible using a mill that produced only six grams of material at one time. An efficient large-scale mechanical process for preparation of the bimetallic particles was necessary to upgrade to a field-scale project and will be discussed in greater detail below.

EXAMPLE

Large Scale

For the scale up, a paint shaker fitted with custom plates to hold the milling canisters was chosen as the mill engine. Tungsten carbide is used as the milling vessel material in most high-energy, small-scale mills because it is extremely durable and does not break down over time or cause the introduction of contaminates into the milling material. The use of an extremely durable milling vessel was not necessary in this case because the introduction of some contaminates would not appreciably affect the reactivity of the metal, thus galvanized steel pipes (purchased from Ace Hardware with internal diameter-5.03 cm, length-17.8 cm) with steel end caps were used. Steel ball bearings (mass-22.3 grams each, volume-1.6 $cm^3$ each) were chosen as the grinding matrix. Since the paint shaker chosen operates at approximately 600 RPMs (as opposed to 1250 RPMs observed for the Spex Centi-prep) longer milling times were necessary.

It has already been shown that, most often, the optimum rate of comminution is observed when milling canisters are filled 40-60% with grinding materials and 10-20% with particulate material, by volume. Optimization was begun within these parameters, however the goal of optimization was not to produce the smallest particle size possible in the least amount of time, rather the goal was to produce activated Pd/Mg bimetallic for the degradation of PCBs in the least amount of time possible.

Optimization of the milling procedure was carried out by varying: the number of balls used, the quantity of Pd/Mg milled, and the length of time that the mill was run. Each variable was isolated and varied while leaving all other parameters constant and set at the middle point of each variable range. For instance, to determine the most effective milling time, the canister was filled 50% with ball bearings and 15% with the palladium and magnesium mixture. The material was milled for varying periods of time then tested for effectiveness at degrading PCBs. The optimum milling time was found and other variables were isolated in a similar manner while keeping the milling time constant.

The activity of each metal produced was tested for PCB dechlorination capacity as follows. Two gram samples of Pd/Mg bimetallic were placed into 20 mL screw cap vials, purchased from I-Chem, along with 10 mL of 6 ppm aqueous 1254 Arochlor solution that was prepared from 5000 ppm Methanol-Arochlor solution, purchased from Accustandard. These solutions were allowed to react while samples were pulled over time to monitor PCB degradation. The PCBs were extracted from solution by adding 5 mL Fischer Scientific HPLC grade Hexane to each vial then shaking the mixture for 1 minute. The Hexane layer was then removed and PCB concentration in the hexane was analyzed with an HP-5890 Series II Plus GC-ECD with an RTX-1 30 meter column, using EPA method 3050B.

Figure 2:
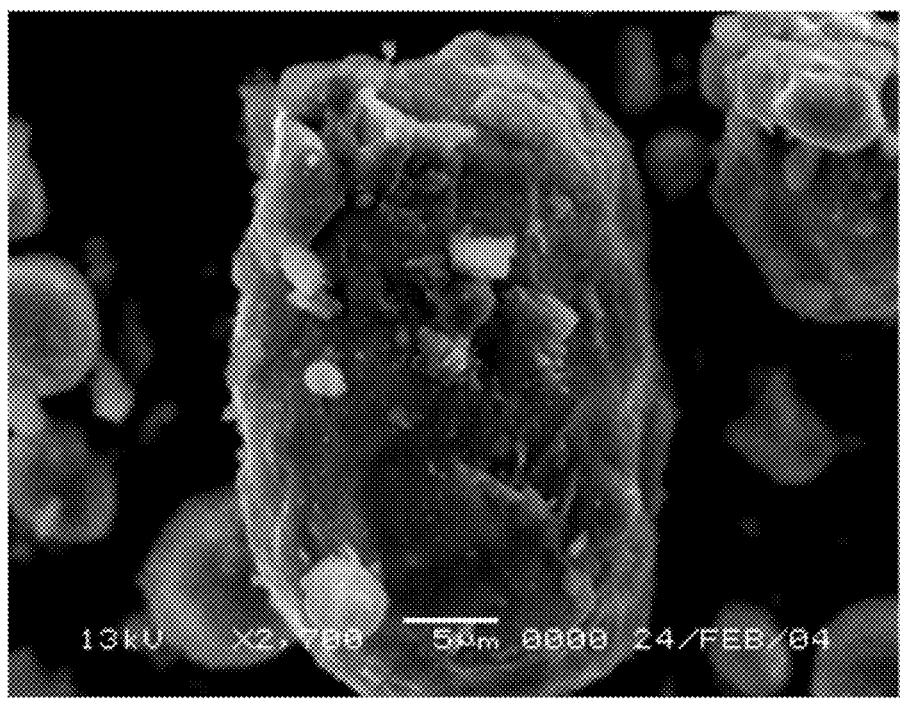
FIG. 2 is an electron micrograph of a bimetallic particle in accordance with the present invention milled for an optimum time period.

With the above-stated optimized milling process, the dechlorination of PCBs in the Arochlor solution was able to be completed within 24 hours of initial contact. Additionally, it was determined that longer milling times actually reduced the rate of dechlorination. As can be seen from the electron micrographs shown in FIG. 1 and FIG. 2, longer milling times cause the palladium (smaller white particles) to be completely embedded into the magnesium (large gray particles), thereby producing less active surface. FIG. 1 shows a bimetallic particle milled for 1.5 hours beyond optimum time. FIG. 2 shows a bimetallic particle milled for optimum time period.

In order to analyze the ability of the bimetallic system to degrade PCBs, a GC system with electron capture detector was used. This allowed for the direct observation of PCB concentration. Since this apparatus is more sensitive, it allowed for a more accurate measurement. The experimental setup was similar to the setup used in the small-scale analysis. Single congeners were used for some studies due to the ease of analysis versus Arochlor mixtures. The study was completed in methanol instead of water to allow for high PCB concentrations.

Using optimized milling time ball-to-mass ratio and canister loading, 0.012, 0.059, 0.083, 0.11, and 0.016% Pd bimetal was prepared and tested for degradation rate as follows:

0.10 g bimetal placed in septa top glass vial
    10 mL 10 ppm Arochlor 1254 methanol solution added
    allowed to react for given period of time
    extracted with toluene
    analyzed on Perkin Elmer Autosystem XL GC-ECD.

Figure 3:
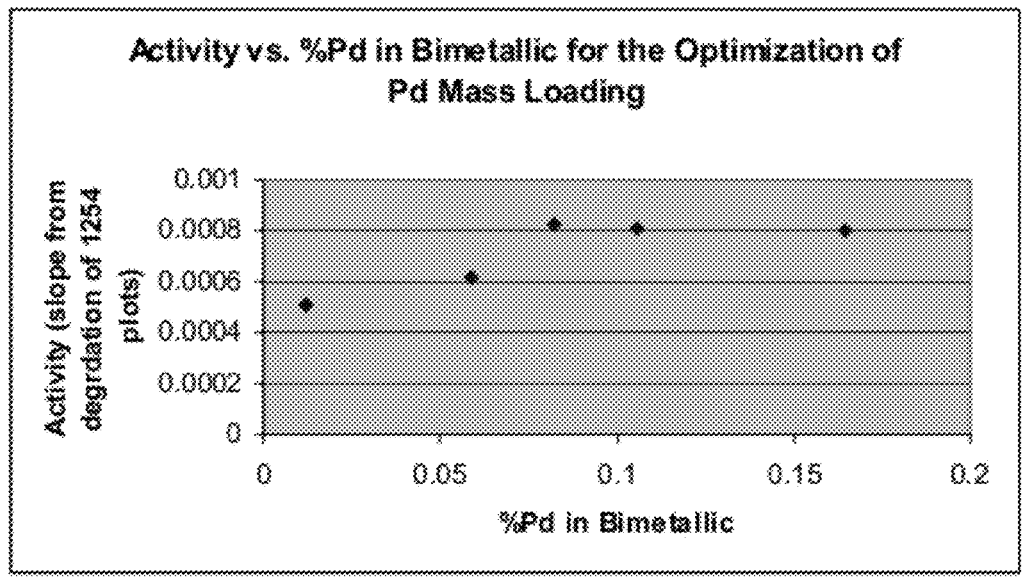
FIG. 3 is a graph showing the activity of the bimetallic particle over different % Pd in the bimetallic for the optimization of Pd mass loading.

It was difficult to quantify the degradation of PCB mixtures since dechlorination is shown to be stepwise through mass spectral studies. However, the change over time in individual parent:dechlorinated-product congener ratio was monitored as a measure of activity, see FIG. 3. The results of the study showed that 0.083% Pd bimetal was found to be the most reactive.

Using optimized Pd loading, ball-to-mass ratio, and canister loading the milling time was varied and activity of product metal was tested for degradation rate as follows:

0.25 g bimetal placed in septa top glass vial
    10 mL 10 ppm PCB-151 methanol solution added
    allowed to react for given time period
    extracted with toluene
    analyzed on Perkin Elmer Autosystem XL GC-ECD
    PCB concentration monitored over time to obtain pseudo first order rate constant.

Figure 4:
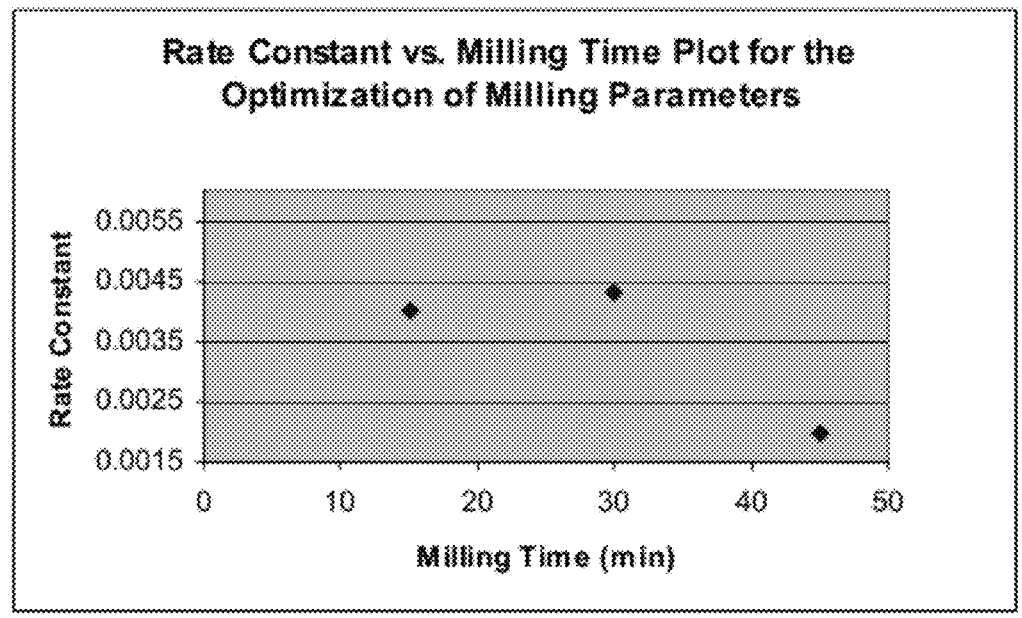
FIG. 4 is a graph showing the rate constant of the bimetallic particle over different milling times for the optimization of milling parameters.

FIG. 4 provides the results that a 30-minute mill time was found to produce the most active bimetal.

Although the present invention has been disclosed in terms of a preferred embodiment, it will be understood that numerous additional modifications and variations could be made thereto without departing from the scope of the invention as defined by the following claims:

We claim:

1. A hydrogenation catalyst comprising,
    a base material capable of generating hydrogen when in contact with a proton donor, wherein said base material has a particle size of 0.1-10 microns and
    a hydrodehalogenation catalyst coated on said base material, wherein said hydrodehalogenation catalyst is a supported catalytic metal including at least one catalytic metal supported on a high surface area conductive or semi-conductive support.

2. The hydrogenation catalyst of claim 1, wherein said catalytic metal is palladium.

3. The hydrogenation catalyst of claim 1, wherein said base material is selected from the group consisting of metals and minerals.

4. The hydrogenation catalyst of claim 3, wherein said base material is a zero-valent metal particle.

5. The hydrogenation catalyst of claim 4, wherein said zero-valent metal particle is selected from the group consisting of zero-valent iron and zero-valent magnesium.

6. The hydrogenation catalyst of claim 4, wherein said zero-valent metal particle is coated with 0.01-15 wt. % said supported catalytic metal.

7. The hydrogenation catalyst of claim 3, wherein said base material is selected from the group consisting of transition metal oxides and iron oxides.

8. The hydrogenation catalyst of claim 3, wherein said catalytic metal is palladium.

9. The hydrogenation catalyst of claim 1, wherein said support is a conductive carbon support.

10. The hydrogenation catalyst of claim 9, wherein said conductive carbon support is graphite.

11. The hydrogenation catalyst of claim 9, wherein 0.1-10% catalytic metal is supported on a conductive carbon support.

* * * * *